United States Patent [19]
Huffer

[11] Patent Number: 5,535,886
[45] Date of Patent: Jul. 16, 1996

[54] HYGIENIC SANITARY TOWEL

[76] Inventor: Richard L. Huffer, 1708 W. County Rd., 400 S., Frankfort, Ind. 46041-7699

[21] Appl. No.: 399,915

[22] Filed: Mar. 7, 1995

[51] Int. Cl.⁶ .............................. B32B 3/04; B32B 3/28
[52] U.S. Cl. ......................... 206/494; 428/121; 428/126; 428/174; 428/180
[58] Field of Search .................... 428/121, 126, 428/174–180; 162/109, 116; 206/494, 491

[56] References Cited

U.S. PATENT DOCUMENTS

Re. 27,453  8/1972  Schutte et al. ................. 162/116
4,637,859  1/1987  Trokhan ........................ 162/109

*Primary Examiner*—Alexander S. Thomas

[57] ABSTRACT

A hygienic sanitary towel of a rectangular planar shape formed of a first outer sheet, a second outer sheet, and a third inner sheet sandwiched between the outer sheets in a stacked registered press-fit relation and with each sheet formed of an absorbent pressed fiber material.

2 Claims, 3 Drawing Sheets

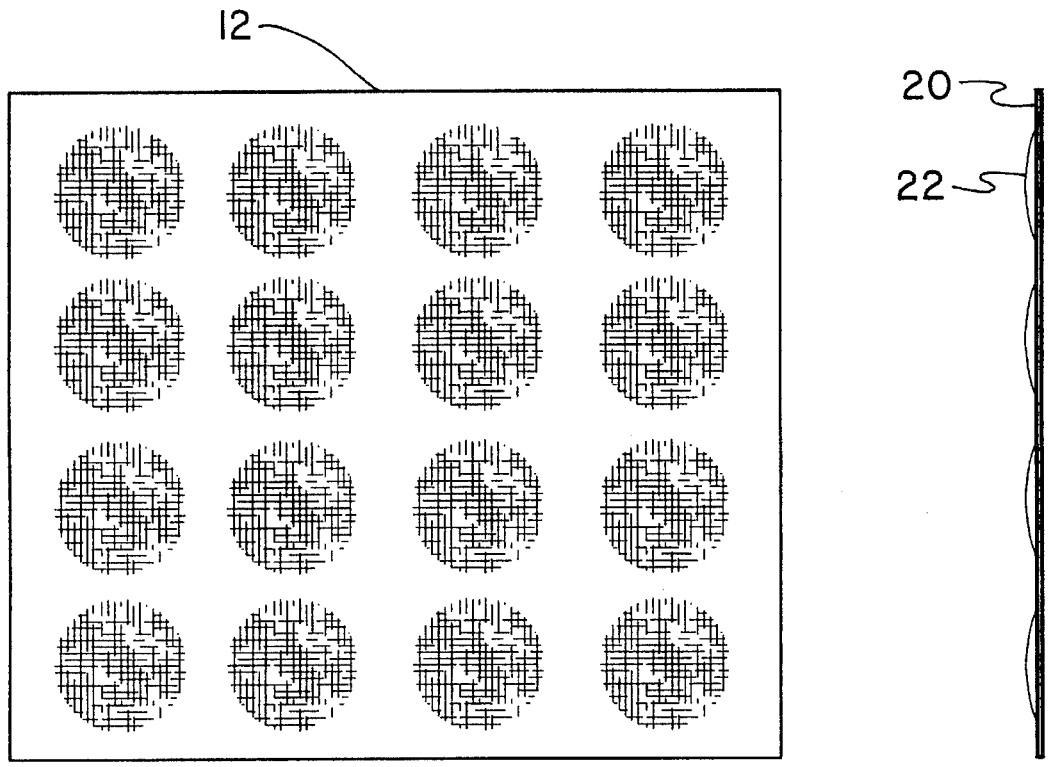
*FIG. 2*    *FIG. 3*
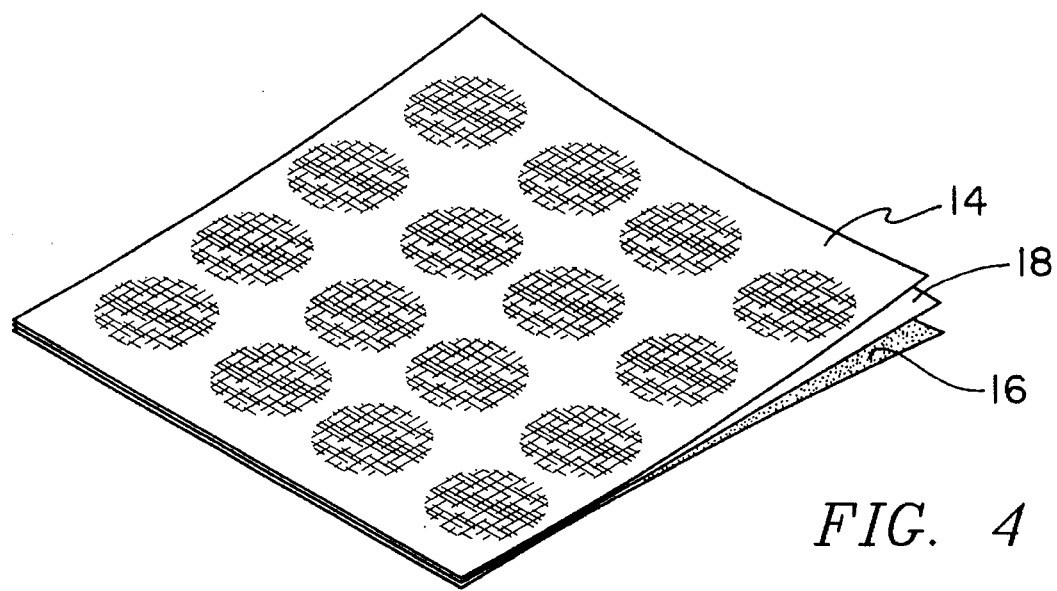
*FIG. 4*

HYGIENIC SANITARY TOWEL

BACKGROUND OF THE INVENTION

1. Field of the Invention

The present invention relates to a hygienic sanitary towel and more particularly pertains to providing a protective barrier between a user's hand and a lavatory surface such as that on a faucet, toilet, urinal and the like with a hygienic sanitary towel.

2. Description of the Prior Art

The use of sanitary towels is known in the prior art. More specifically, sanitary towels heretofore devised and utilized for the purpose of shielding a user from direct contact with a surface are known to consist basically of familiar, expected and obvious structural configurations, notwithstanding the myriad of designs encompassed by the crowded prior art which have been developed for the fulfillment of countless objectives and requirements.

By way of example, U.S. Pat. No. 288,363 to Wallstrom discloses a sanitary towel. U.S. Pat. No. 3,570,943 to Olsson discloses a sanitary towel. U.S. Pat. No. 3,613,688 to Dahisten discloses a sanitary towel. U.S. Pat. No. 4,333,465 to Wiegner discloses a hygienic sanitary towel. U.S. Pat. No. 4,662,876 to Wiegner discloses a hygienic sanitary towel. U.S. Pat. No. 5,004,637 to Liao discloses a sanitary tearing towel.

While these devices fulfill their respective, particular objective and requirements, the aforementioned patents do not describe a hygienic sanitary towel that allows a user to avoid making direct contact with possible contaminated surfaces in lavoratories or the like and provides a built-in gripping surface.

In this respect, the hygienic sanitary towel according to the present invention substantially departs from the conventional concepts and designs of the prior art, and in doing so provides an apparatus primarily developed for the purpose of providing a protective barrier between a user's hand and a lavatory surface such as that on a faucet, toilet, urinal and the like.

Therefore, it can be appreciated that there exists a continuing need for new and improved hygienic sanitary towel which can be used for providing a protective barrier between a user's hand and a lavatory surface such as that on a faucet, toilet, urinal and the like. In this regard, the present invention substantially fulfills this need.

SUMMARY OF THE INVENTION

In the view of the foregoing disadvantages inherent in the known types of sanitary towels now present in the prior art, the present invention provides an improved hygienic sanitary towel. As such, the general purpose of the present invention, which will be described subsequently in greater detail, is to provide a new and improved hygienic sanitary towel and method which has all the advantages of the prior art and none of the disadvantages.

To attain this, the present invention essentially comprises, in combination, a plurality of planar flexible towels. Each towel has rectangular shape with a length of between about 4½ inches to 4⅝ inches and a width of between about 4¼ inches to 4½ inches. Each towel includes a first outer sheet, a second outer sheet, and a third inner sheet sandwiched between the outer sheets in a stacked registered press-fit relation. Each sheet of each towel is formed of an absorbent paper material. The first sheet of each towel has an outboard surface with a plurality of dome-shaped textured regions protruding therefrom in a matrix-like configuration for allowing a user a firm grip. Each towel further has a pair of parallel linear folds formed longitudinally thereon and with the folds defining a pair of outboard sections with an inboard section therebetween. The towels are positionable in a stacked configuration with an outboard section of a given towel interposed between an outboard and an inboard section of an adjacent towel.

A rigid box-shaped plastic towel dispenser is provided for receiving and holding the stacked configuration of towels therein for subsequent dispensation. The towel dispenser has a planar back wall with an inboard surface, an outboard surface, and a periphery interconnecting the surfaces formed of a top edge, a bottom edge, and a pair of opposed side edges extended therebetween, a latch formed on the midpoint of top edge, and a plurality of through holes formed thereon for receipt of fasteners for securing the back wall to a recipient surface such as a wall. The towel dispenser further has a lid hingably coupled to the back wall near the bottom edge thereof. The lid includes a planar front wall with a border extended peripherally outwards therefrom to define an interior for receiving the stacked configuration of towels and an opening for allowing access to the interior for removal or replacement of towels. The border of the lid is formed of a planar top wall, a planar bottom wall, and a pair of opposed planar side walls extended therebetween. The front wall of the lid additionally includes a port thereon for viewing the stacked configuration of towels within the interior. The top wall includes key-actuated lock coupled thereto. The lock is removably securable to the latch on the back wall to secure the lid to the back wall and thereby seal the opening while simultaneously placing the stacked configuration of towels in an orientation for use. The bottom wall additionally includes an elongated slot formed thereon for allowing an individual towel to be dispensed from the interior.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved hygienic sanitary towel which has all the advantages of the prior art sanitary towels and none of the disadvantages.

It is another object of the present invention to provide a new and improved hygienic sanitary towel which may be easily and efficiently manufactured and marketed.

It is a further object of the present invention to provide a new and improved hygienic sanitary towel which is of durable and reliable construction.

An even further object of the present invention is to provide a new and improved hygienic sanitary towel which is susceptible of a low cost of manufacture with regard to both materials and labor, and which accordingly is then susceptible of low prices of sale to the consuming public, thereby making such a hygienic sanitary towel economically available to the buying public.

Still yet another object of the present invention is to provide a new and improved hygienic sanitary towel which provides in the apparatuses and methods of the prior art some of the advantages thereof, while simultaneously overcoming some of the disadvantages normally associated therewith.

Even still another object of the present invention is to provide a new and improved hygienic sanitary towel for providing a protective barrier between a user's hand and a lavatory surface such as that on a faucet, toilet, urinal and the like.

Lastly, it is an object of the present invention to provide a new and improved hygienic sanitary towel of a rectangular planar shape formed of a first outer sheet, a second outer sheet, and a third inner sheet sandwiched between the outer sheets in a stacked registered press-fit relation and with each sheet formed of an absorbent pressed fiber material.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a plan view of the towel of the present invention.

FIG. 3 is a side-elevational view of the towel of the present invention.

FIG. 4 is a perspective view of the towel of the present invention.

The same reference numerals refer to the same parts through the various Figures.

DESCRIPTION OF THE PREFERRED EMBODIMENT

Figure 1:
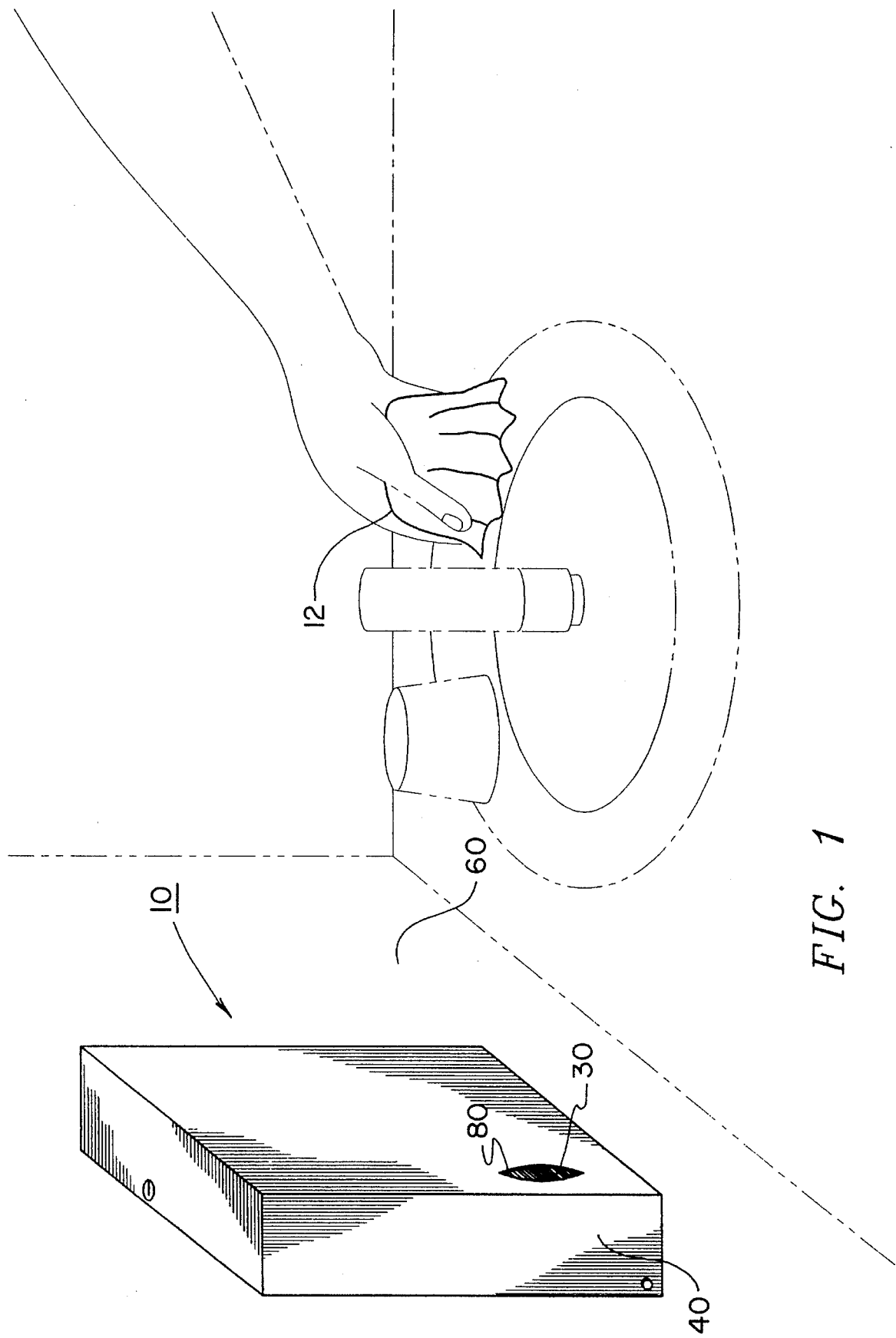
FIG. 1 is a perspective view of the preferred embodiment constructed in accordance with the principles of the present invention in use for shielding a user's hand on a lavatory faucet.

With reference now to the drawings, and in particular, to FIG. 1 thereof, the preferred embodiment of the new and improved hygienic sanitary towel embodying the principles and concepts of the present invention and generally designated by the reference number 10 will be described.

The present invention is comprised of a plurality of components. In their broadest context, such components include a plurality of towels and a towel dispenser. Such components are individually configured and correlated with respect to each other to provide the intended function.

Figure 6:
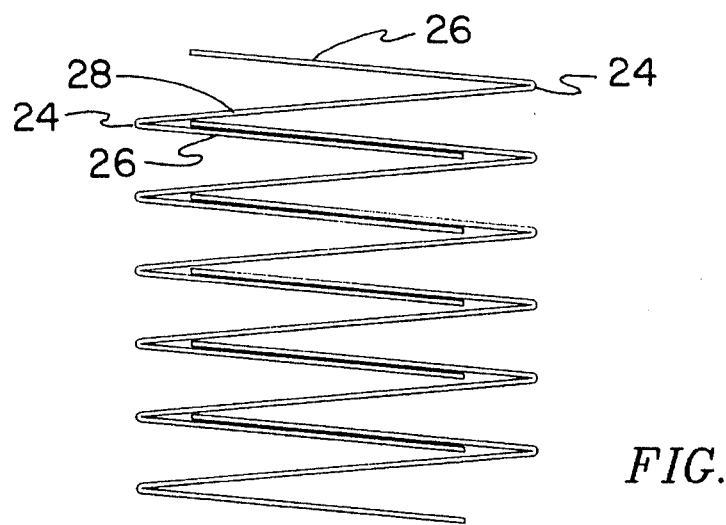
FIG. 6 is a side-elevational view of the positioning of the towels in a folded stacked configuration for use.

Specifically, the present invention includes a plurality of planar and flexible towels. The towels are used for shielding a user's hand or other body part from direct contact with a possible contaminated or dirty surface. As shown in FIG. 2, each towel 12 has a rectangular planar shape. The length of the towel as measured longitudinally therealong is between about 4½ inches to about 4⅝ inches. The width of the towel as measured transversely therealong is between about 4¼ inches to about 4½ inches. As best illustrated in FIG. 4, each towel has a three-ply construction which includes a first outer sheet 14, a second outer sheet 16, and a third inner sheet 18 sandwiched between the outer sheets. The sheets are coupled together in a stacked and registered press-fit relation that creates a frictional coupling. Each sheet of each towel is formed of an absorbent paper or fibrous material. The sheets are further formed with sufficient thickness such that they do not readily tear when is use when wet or dry. Furthermore, the first sheet 14 of each towel has an outboard surface 20 with a plurality of dome-shaped textured regions 22 protruding therefrom as shown in FIG. 3. Each protrusion extends perpendicularly outwards a distance no greater than the nominal thickness of the sheet. The textured regions of the first sheet are formed in a matrix-like configuration consisting of six transverse rows and four longitudinal columns. Thus, twenty-four textured regions are provided on the first sheet and allow a user a firm grip of the towel. When the first sheet is grasped, the second outer sheet 16 is positionable in facing contact with a recipient surface. Each textured region has a cross-stitched type structure with alternating high and low areas in both longitudinal and transverse directions that are parallel with the respective longitudinal and transverse directions of the towel itself. This cross-stitch type structure provides a suitable gripping surface for grasping with the fingers of a hand. Furthermore, as shown in FIG. 6, each towel has a pair of parallel linear folds 24 formed longitudinally thereon. The folds define a pair of rectangular outboard sections 26 with a rectangular inboard section 28 therebetween. The inboard section has a width greater than the outboard sections.

The towels are positionable in a stacked configuration 30 as shown in FIG. 1. An outboard section of a given towel is interposed between an outboard and an inboard section of an adjacent towel as best illustrated in FIG. 6. This places each towel in a position for ready dispersement without adversely affecting the relative position of the remaining towels in the stack.

Figure 5:
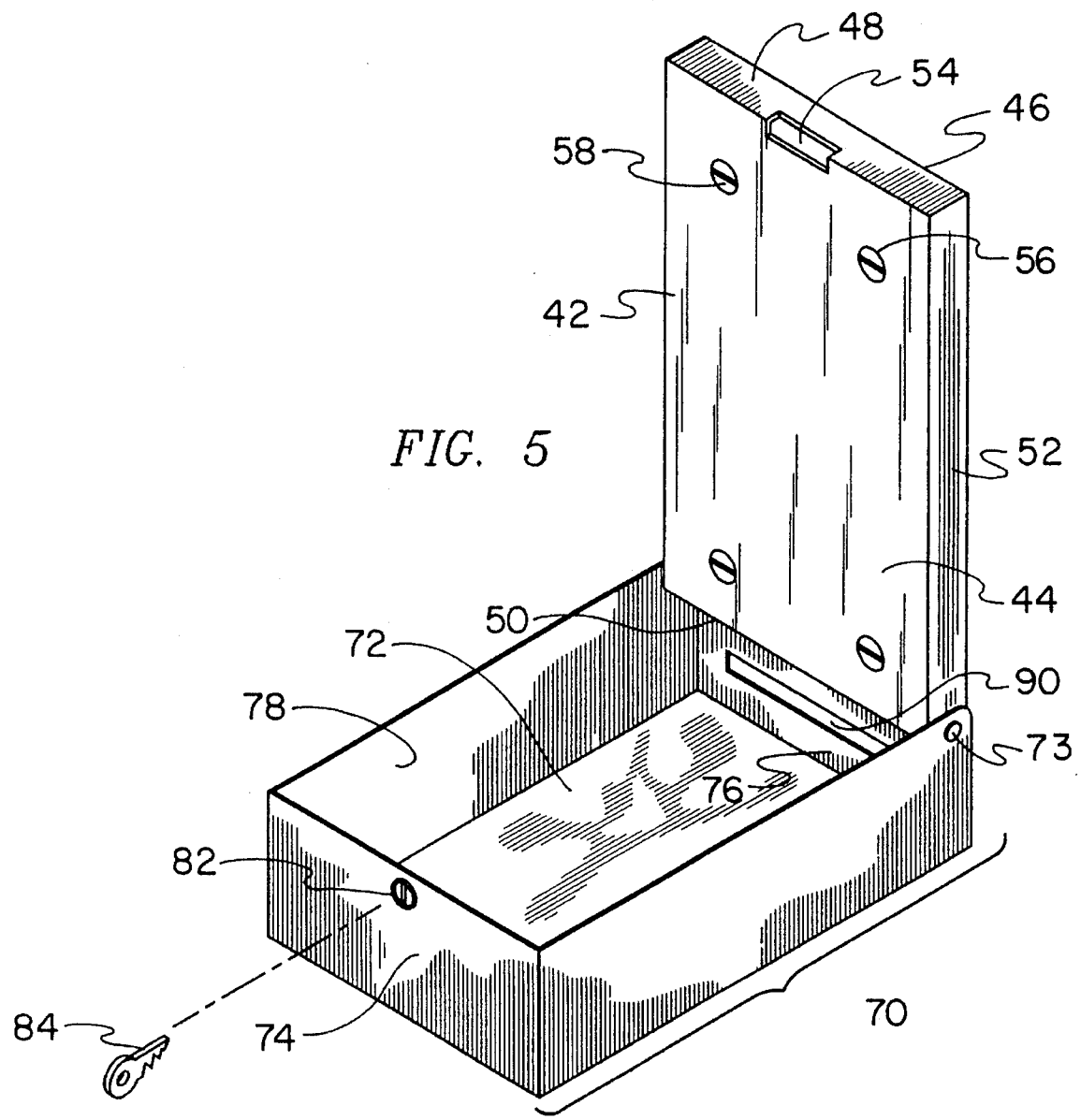
FIG. 5 is a perspective view of the towel dispenser of the present invention.

In addition, a towel dispenser 40 is provided as shown in FIG. 5. The towel dispenser is formed of a rigid plastic material of a white color and has a box-like shape. The towel dispenser is used for receiving and holding the stacked configuration 30 of towels therein for subsequent dispensation for use. The towel dispenser has a planar rectangular back wall 42. The back wall has an inboard surface 44, an outboard surface 46, and a periphery interconnecting the surfaces. The periphery is formed of a top edge 48, a bottom edge 50, and a pair of opposed side edges 52 extended therebetween. A latch 54 is formed on the midpoint of the top edge and extends a distance upon the inboard surface. In addition, four through holes 56 are formed on the back wall near each corner. The through holes are used for receiving screws 58, nails, or other similar fasteners for securing the back wall to a recipient surface in a readily accessible position such as a wall 60 as shown in FIG. 1.

The towel dispenser also has a lid 70. The lid is hingably coupled to the back wall 42 near the bottom edge 50 thereof with hinge pins 73. The lid includes a planar rectangular front wall 72 with a border extended peripherally outwards therefrom. The outer extent of the border is positionable in facing contact with the periphery of the back wall 42. The border thus defines an interior for receiving the stacked configuration 30 of towels and provides an opening for allowing access to the interior for removal or replacement of towels as needed. The border is formed of a planar rectangular top wall 74, a planar rectangular bottom wall 76, and a pair of opposed planar rectangular side walls 78 extended therebetween. The front wall additionally includes an elongated port 80 formed thereon near the bottom wall 76. The port is used for viewing the stacked configuration 30 of towels in order to determine whether the dispenser needs refilling when placed in use. The lid also includes a lock 82 coupled to the top wall 74. The lock is actuated with key 84. The lock is removably securable to the latch 54 on the back wall to hold the lid against the back wall and thereby seal the opening. When the lid is locked to the back wall, the stacked configuration of towels is simultaneously placed in an orientation for use. To allow a user to access a towel for use, the bottom wall additionally includes an elongated slot 90 formed thereon. The slot enables an individual towel to be dispensed from the interior of the towel dispenser. The slot has a length greater than the extent of the towel for allowing dispensation of a towel without it being wrinkled or torn.

The present invention is used to provide a protective barrier between a user's hand and a recipient surface such as a water faucet handle, lavatory soap dispenser, flush handles on urinals and toilets, and like surfaces which the public uses. The present invention thus shields a user from being infected by direct contact with many common viruses such as strains of common colds and other serious viruses which can be acquired by touching a contaminated surface and then subsequently touching the nose or eyes. This can occur even after washing, because a user must again touch a faucet handle to turn off the water such as in a majority of restrooms. The present invention is mounted for use near a wash basin or placed over a lavatory handle or faucet. A towel may then be readily dispensed prior contacting possible contaminated surfaces in a lavatory.

The towel of the present invention can be made of a brown recycled paper commonly used for hand drying in restrooms, or a more suitable material to protect the user as intended. This material may be possibly a little thicker or less absorbent than conventional paper towels in restrooms.

The towels are tri-folded and dispensed the same way larger towels are packaged and dispensed. In the preferred embodiment, the dispenser is made of a heavy white plastic and is 15½ inches long by about 11 inches wide by about 4¾ inches thick. The dispenser has a simple lock at the top which comes either with a plastic or metal key. The front of the dispenser is hinged with simple pins which allow the front to drop down for easy loading of the tri-folded paper towels. The present invention would help address the publics' and consumers' awareness of safety and health in public areas such as lavatories. The paper towels of the present invention may also be carried in a portable type configuration.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A hygienic sanitary towel and dispenser apparatus comprising, in combination:

a plurality of planar flexible towels, each towel having a having rectangular shape with a length of between about 4½ inches to 4⅝ inches and a width of between about 4¼ inches to 4½ inches, each towel including a first outer sheet, a second outer sheet, and a third inner sheet sandwiched between the outer sheets in a stacked registered press-fit relation, each sheet of each towel formed of an absorbent paper material and with the first sheet of each towel having an outboard surface with a plurality of dome-shaped textured regions protruding therefrom in a matrix-like configuration for allowing a user a firm grip, each towel further having a pair of parallel linear folds formed longitudinally thereon and with the folds defining a pair of outboard sections with an inboard section therebetween and with the towels positionable in a stacked configuration with an outboard section of a given towel interposed between an outboard and an inboard section of an adjacent towel;

a rigid box-shaped plastic towel dispenser for receiving and holding the stacked configuration of towels therein for subsequent dispensation, the towel dispenser having a planar back wall with an inboard surface, an outboard surface, and a periphery interconnecting the surfaces formed of a top edge, a bottom edge, and a pair of opposed side edges extended therebetween, a latch formed on the midpoint of top edge, and a plurality of through holes formed thereon for receipt of fasteners for securing the back wall to a recipient surface such as a wall, the towel dispenser further having a lid hingably coupled to the back wall near the bottom edge thereof, the lid including a planar front wall with a border extended peripherally outwards therefrom to define an interior for receiving the stacked configuration of towels and an opening for allowing access to the interior for removal or replacement of towels, the border formed of a planar top wall, a planar bottom wall, and a pair of opposed planar side walls extended therebetween, the front wall additionally including a port thereon for viewing the stacked configuration of towels within the interior, the top wall additionally including a key-actuated lock coupled thereto and with the lock removably securable to the latch on the back wall to secure the lid to the back wall and thereby seal the opening while simultaneously placing the stacked configuration of towels in an orientation for use, the bottom wall additionally including an elongated slot formed thereon for allowing an individual towel to be dispensed from the interior wherein the first outer sheet is shaped so as to define a plurality of dome-shaped textured regions all projecting in a single direction from an exterior surface thereof, the textured regions each having a cross-stitched structure defining alternating high and low elongated areas extending in both longitudinal and transverse directions along only the textured regions, with areas between the textured regions not having the cross-stitched structure.

2. A hygienic sanitary towel of a rectangular shape comprising:

a first outer sheet having an interior surface and an exterior surface;

a second outer sheet positioned in a stacked and registered orientation over the first outer sheet;

a third inner sheet interposed between the first outer sheet and the second outer sheet, the third inner sheet being positioned in a stacked and registered orientation over the first and second outer sheets, the third inner sheet being positioned in an abutting orientation with the interior surface of the first outer sheet;

wherein the first outer sheet is shaped so as to define a plurality of dome-shaped textured regions all projecting in a single direction from the exterior surface of the first outer sheet, the textured regions each having a cross-stitched structure defining alternating high and low elongated areas extending in both longitudinal and transverse directions along only the textured regions, with areas between the textured regions not having the cross-stitched structure.

* * * * *